(12) United States Patent
Jackson et al.

(10) Patent No.: US 11,078,489 B2
(45) Date of Patent: Aug. 3, 2021

(54) METHODS AND COMPOSITIONS FOR BACKSCATTERING INTERFEROMETRY

(71) Applicant: Base Pair Biotechnologies, Inc., Pearland, TX (US)

(72) Inventors: George W. Jackson, Pearland, TX (US); Darryl Bornhop, Nashville, TN (US)

(73) Assignee: Base Pair Biotechnologies, Inc., Pearland, TX (US)

( * ) Notice: Subject to any disclaimer, the term of this patent is extended or adjusted under 35 U.S.C. 154(b) by 0 days.

(21) Appl. No.: 15/959,389

(22) Filed: Apr. 23, 2018

(65) Prior Publication Data

US 2019/0119681 A1    Apr. 25, 2019

Related U.S. Application Data

(62) Division of application No. 15/065,837, filed on Mar. 9, 2016, now Pat. No. 9,963,706.

(60) Provisional application No. 62/130,583, filed on Mar. 9, 2015.

(51) Int. Cl.
*C07H 21/04* (2006.01)
*C12N 15/115* (2010.01)
*G01N 33/53* (2006.01)
*G01N 21/47* (2006.01)
*G01N 33/542* (2006.01)

(52) U.S. Cl.
CPC .......... *C12N 15/115* (2013.01); *G01N 21/47* (2013.01); *G01N 33/5308* (2013.01); *G01N 33/542* (2013.01); *C12N 2310/16* (2013.01); *C12N 2310/531* (2013.01); *G01N 2021/4709* (2013.01)

(58) Field of Classification Search
CPC .................................................. C12N 15/115
See application file for complete search history.

(56) References Cited

U.S. PATENT DOCUMENTS

2016/0274095 A1 *  9/2016  Toulme .................. C07H 21/02

* cited by examiner

*Primary Examiner* — Kimberly Chong
(74) *Attorney, Agent, or Firm* — Equip LG; Christopher Quan

(57) ABSTRACT

The present invention relates to methods and compositions for enhancing backscattering interferometry (BSI) in detection of biomolecular interactions, particularly to methods and compositions for enhancing BSI utilizing label-free aptamers, and more particularly to methods and compositions for enhancing BSI utilizing high conformational change aptamers, which may change in conformation when the aptamers bind to their target molecules.

7 Claims, 3 Drawing Sheets

Specification includes a Sequence Listing.

METHODS AND COMPOSITIONS FOR BACKSCATTERING INTERFEROMETRY

CROSS-REFERENCE TO RELATED APPLICATIONS

This application is a divisional of U.S. utility patent application Ser. No. 15/065,837, filed Mar. 9, 2016, entitled "METHODS AND COMPOSITIONS FOR BACKSCATTERING INTERFEROMETRY", which claims the benefit of U.S. provisional patent application Ser. No. 62/130,583, filed Mar. 9, 2015, entitled "METHODS AND COMPOSITIONS FOR BACKSCATTERING INTERFEROMETRY", the full contents of all of such applications are hereby incorporated by reference in their entireties.

FIELD OF THE INVENTION

This invention relates to methods and compositions for enhancing backscattering interferometry (BSI), particularly to methods and compositions for enhancing BSI utilizing label-free aptamers, and more particularly to methods and compositions for enhancing BSI utilizing high conformational change aptamers.

SEQUENCE LISTING

Deoxyribonucleic acid (DNA) sequences, which are disclosed in the ASCII text file entitled "P1025US02_ST25.txt", created on Jul. 17, 2020 and of 437 bytes in size, which is incorporated by reference in its entirety.

BACKGROUND OF THE INVENTION

Aptamers are single-strand DNA or RNA molecules that can be designed and produced rapidly and inexpensively to bind with high affinity and specificity to a desired target molecule. Proteins, peptides, and small molecules are all suitable targets. Aptamers can assume a variety of shapes. Because of their versatility, aptamers have a vast array of applications which include but are not limited to use as sensors, therapeutic tools, and cellular process regulators, as well as to guide drugs to their specific cellular targets. Aptamers are generally a good substitute for applications requiring an antibody because aptamers can be designed and produced rapidly, inexpensively, and most importantly, in vitro. DNA aptamers are stable for long periods without the strict storage requirements of antibodies. Perhaps most importantly as compared to antibodies, once identified, aptamers can be produced by purely synthetic means; that is, no organisms, cell culture or biological expression system is required. As such, unlike antibodies, aptamers reagents experience virtually no lot-to-lot variability. Further, facile modifications can be made to aptamers during synthesis that can confer nuclease stability of the molecules in serum for in vivo and diagnostic applications.

Characterization of the interaction between aptamers and their target molecules is of interest to the scientific community, because these interactions have broad applications ranging from drug delivery to metabolite detection. Two common methods of measuring binding affinity are surface plasmon resonance (SPR) and biolayer interferometry (BLI). SPR measures the localized change in the refractive index (RI) near the surface of a substrate in order to detect binding and has been used in a multiplex format. However, SPR is a heterogeneous method that requires complicated surface chemistry, immobilization, possible modification of one of the species being examined, and expensive gold-plated slides. Biolayer interferometry is a label-free technology for measuring biomolecular interactions. It is an optical analytical technique that analyzes the interference pattern of white light reflected from two surfaces: a layer of immobilized protein on the biosensor tip, and an internal reference layer. However, BLI also relies on surface immobilization and suffers from similar problems to SPR.

SUMMARY OF THE INVENTION

The present invention relates to methods and compositions for enhancing backscattering interferometry (BSI) in detection of biomolecular interactions, particularly to methods and compositions for enhancing BSI utilizing label-free aptamers, and more particularly to methods and compositions for enhancing BSI utilizing high conformational change aptamers, which may change in conformation when the aptamers bind to their target molecules.

In one aspect of the invention, methods and compositions for enhancing BSI may employ label-free aptamers which may generally exhibit a large conformational change between their free, unbound state and their bound state when bound to their target molecule. In general, BSI signals may be detecting when a molecule undergoes changes in conformation, hydration shell, hydration, etc., and thus may detect a conformational change of an aptamer upon binding a target, as well as any changes in hydration, hydration shell, etc. that may also occur.

In some exemplary embodiments, at least partially self-complementary aptamers may be utilized to enhance BSI signal. In general, partially self-complementary aptamers may be designed to partially hybridize with themselves in the absence of their target molecule and dehybridize when binding to their target molecule. This hybridization-dehybridization may thus be utilized to generate a large conformational change in the aptamer depending on the presence or absence of target molecules.

In some exemplary embodiments, the at least partially self-complementary aptamers may be designed as nucleic acid hairpins which may generally include a self-hybridizing stem region and a non-self-hybridizing loop region. In general, the aptamers may also further include a region which may bind to a target molecule, which may form at least part of the stem region, the loop region and/or both.

The stem region may be designed to form a predetermined number of Watson-Crick hybridizing pairs in the hairpin conformation of the aptamer. In general, the higher the number of hybridizing pairs, the greater the amount of energy is required to break the hybridization to elicit a conformational change. This may generally correlate with the strength of binding between the aptamer and its target molecule, as stronger binding to a target molecule may generally increase the likelihood of breaking the hybridization in the stem region.

In another aspect of the invention, the stem region length may be tailored to modulate the sensitivity of the aptamer to its target molecule. In general, a longer stem region may be less likely to dehybridize in the presence of a target molecule and thus the aptamer may be less sensitive to its presence.

In yet another aspect of the invention, BSI signal may be improved in an intermolecular system, such as by utilizing an aptamer and a separate at least partially complementary nucleic acid. In some exemplary embodiments, the separate nucleic acid may hybridize to the aptamer in the absence of the target molecule and be dehybridized in the presence of the target molecule due to a conformational change in the aptamer and/or due to the target binding region being shared with the complementary region on the aptamer.

The present invention together with the above and other advantages may best be understood from the following detailed description of the embodiments of the invention and as illustrated in the drawings.

DETAILED DESCRIPTION OF THE INVENTION

Figure 1:
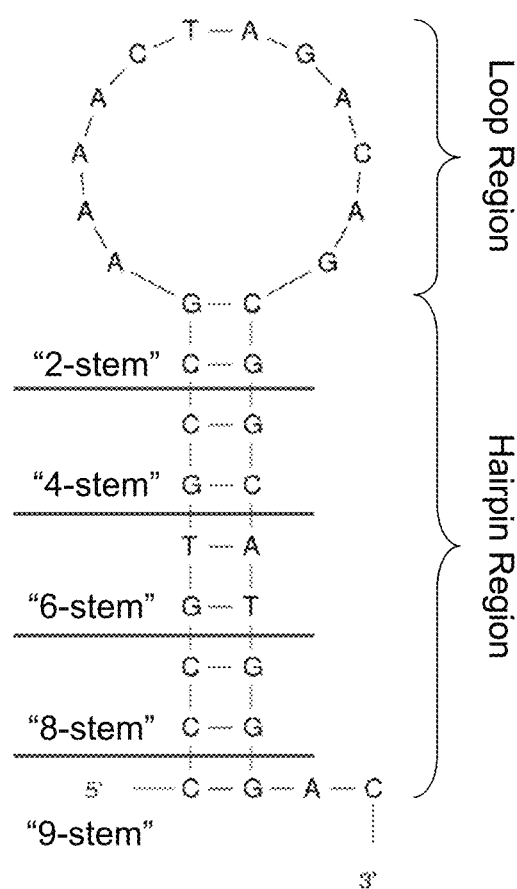
FIG. 1 illustrates a schematic of an embodiment of a hairpin aptamer with a variable length stem region and a loop region.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

An "aptamer" refers to an artificial and/or non-naturally occurring nucleic acid molecule that is capable of binding to a particular molecule of interest or a target with high affinity and specificity. Aptamers are typically generated by a sequential selection process from a randomized pool of artificial candidate sequences referred to as systematic evolution of ligands by exponential enrichment (SELEX). Aptamers may generally include, but are not limited to, single-stranded nucleic acid, such as, for example, single-stranded DNA (ssDNA), single-stranded RNA (ssRNA), and/or a combination thereof; at least a portion of double-stranded nucleic acid, such as, for example, double-stranded DNA (dsDNA), double-stranded RNA (dsRNA), and/or combinations thereof; modified nucleotides and/or other useful molecules, moieties, and/or other functional chemical components, or combinations thereof; or combinations thereof or similar. Aptamers may also include non-natural nucleotides and nucleotide analogs. Aptamers generally have specific binding regions which are capable of forming complexes with an intended target molecule in an environment wherein other substances in the same environment are not complexed to the aptamer. The specificity of the binding is defined in terms of the comparative dissociation constants (Kd) of the aptamer for its ligand and/or target molecule as compared to the dissociation constant of the aptamer for other materials in the environment or unrelated molecules in general. Typically, the Kd for the aptamer with respect to its ligand and/or target molecule may be at least about 10-fold less than the Kd for the aptamer with unrelated material or accompanying material in the environment, for example. More for example, the Kd may be at least about 50-fold less, even more for example, at least about 100-fold less, and still even more for example, at least about 200-fold less.

An aptamer may typically be between about 10 and about 300 nucleotides in length. More commonly, an aptamer may be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and may be metabolized in a manner similar to naturally occurring nucleotides. Unless otherwise indicated, a particular nucleic acid sequence also implicitly encompasses conservatively modified variants thereof (e.g., degenerate substitutions) and complementary sequences as well as the sequence explicitly indicated. As an example, degenerate substitutions may be achieved by generating sequences in which one or more positions of the aptamer is substituted with mixed-base and/or deoxyinosine residues. Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used herein interchangeably with oligonucleotide, gene, cDNA, and mRNA encoded by a gene.

In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, 5-Trifluoromethyl-2'-deoxyuridine-5'-Triphosphate and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base.

The present invention relates to methods and compositions for enhancing backscattering interferometry (BSI) in detection of biomolecular interactions, particularly to methods and compositions for enhancing BSI utilizing label-free aptamers, and more particularly to methods and compositions for enhancing BSI utilizing high conformational change aptamers, which may change in conformation when the aptamers bind to their target molecules.

Backscattering interferometry (BSI) is a label-free, free-solution technology that generally allows for a broad range of binding affinities (e.g. pM-mM) to be measured in a matter of hours without a priori knowledge of the binding system. Generally, to analyze a system using BSI, a laser is passed through a glass capillary containing the binding system in solution, and the light reflected back from the capillary creates a defined set of fringes. Several sections of this fringe pattern may have uniform fringes, and the intensity of the fringes shows a signal spatial frequency. By watching how the phase of that single spatial frequency shifts over time BSI can quantitatively measure change in refractive index in the binding system. Because the BSI signal is a product of inherent properties of the sample, there is generally no need for surface-immobilization or labeling to characterize a binding interaction quantitatively. Some of the factors that affect the refractive index (RI) of a binding system are changes in conformation, waters of hydration, and dipole moment.

In one aspect of the invention, methods and compositions for enhancing BSI may employ label-free aptamers which may generally exhibit a large conformational change between their free, unbound state and their bound state when bound to their target molecule. In general, BSI signals may be detecting when a molecule undergoes changes in conformation, hydration shell, hydration, etc., and thus may detect a conformational change of an aptamer upon binding a target, as well as any changes in hydration, hydration shell, etc. that may also occur.

In some exemplary embodiments, at least partially self-complementary aptamers may be utilized to enhance BSI signal. FIG. 1 illustrates a schematic of an example of an at least partially self-complementary aptamer. In general, partially self-complementary aptamers may be designed to partially hybridize with themselves in the absence of their target molecule and dehybridize when binding to their target molecule. This hybridization-dehybridization may thus be utilized to generate a large conformational change in the aptamer depending on the presence or absence of target molecules.

In some exemplary embodiments, the at least partially self-complementary aptamers may be designed as nucleic acid hairpins which may generally include a self-hybridizing stem region and a non-self-hybridizing loop region, as illustrated in FIG. 1. In general, the aptamers may also further include a region which may bind to a target molecule, which may form at least part of the stem region, the loop region and/or both.

The stem region may be designed to form a predetermined number of Watson-Crick hybridizing pairs in the hairpin conformation of the aptamer, as illustrated with the schematic in FIG. 1 showing, for example, stem lengths of 2, 4, 6, 8 and 9 nucleotides. Any other appropriate stem length may also be utilized. In general, the higher the number of hybridizing pairs, the greater the amount of energy is required to break the hybridization to elicit a conformational change. This may generally correlate with the strength of binding between the aptamer and its target molecule, as stronger binding to a target molecule may generally increase the likelihood of breaking the hybridization in the stem region. However, in some embodiments, such as with larger target molecules, for example, the stem region may be forced to dehybridize for the aptamer to bind to its target. In such embodiments, longer stem regions may be utilized to increase the BSI signal. Without being bound to any particular theory, this may be due to the increase in hydration of the aptamer due to its longer length coupled with the stem region dehybridizing in order for any binding to take place.

Figure 1A:
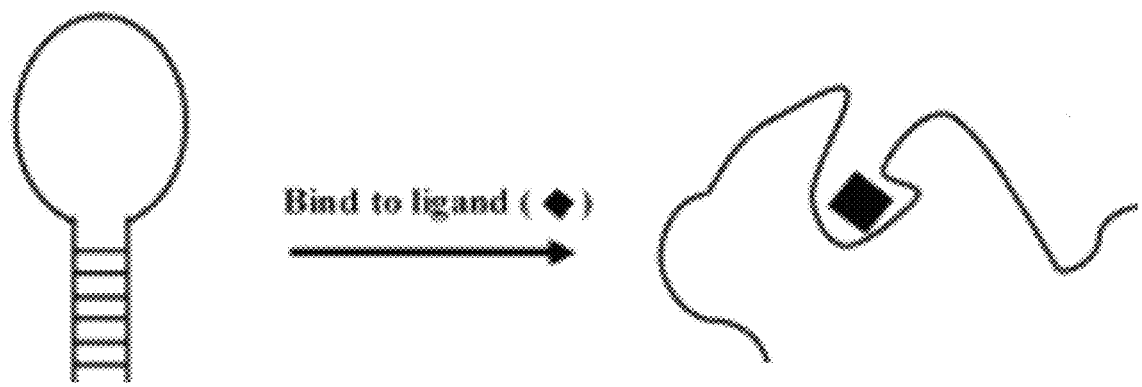
FIG. 1a illustrates binding of a hairpin aptamer to a ligand and associated conformation change.

FIG. 1a illustrates a hairpin aptamer binding to a target molecule, shown as a ligand. As illustrated, the hairpin aptamer may undergo a significant conformation change, as shown with the difference in shape, when the ligand binds and the stem region dehybridizes.

In another aspect of the invention, the stem region length may be tailored to modulate the sensitivity of the aptamer to its target molecule. In general, a longer stem region may be less likely to dehybridize in the presence of a target molecule and thus the aptamer may be less sensitive to its presence. In some embodiments, mismatches, accessory loop regions, and/or other nucleic acid formations may also be introduced to modulate the hybridization of the stem region and thus, for example, the melting temperature and/or the Gibbs free energy ($\Delta G$) of the hybridization.

Figure 1B:
FIG. 1b illustrates an aptamer with a complementary nucleic acid binding to a ligand and displacing the complementary nucleic acid due to conformation change.

In yet another aspect of the invention, BSI signal may be improved in an intermolecular system, such as by utilizing an aptamer and a separate at least partially complementary nucleic acid. In some exemplary embodiments, the separate nucleic acid may hybridize to the aptamer in the absence of the target molecule and be dehybridized in the presence of the target molecule due to a conformational change in the aptamer and/or due to the target binding region being shared with the complementary region on the aptamer, as illustrated in FIG. 1b.

Example of a Hairpin Aptamer System Binding to Tenofovir

Figure 2:
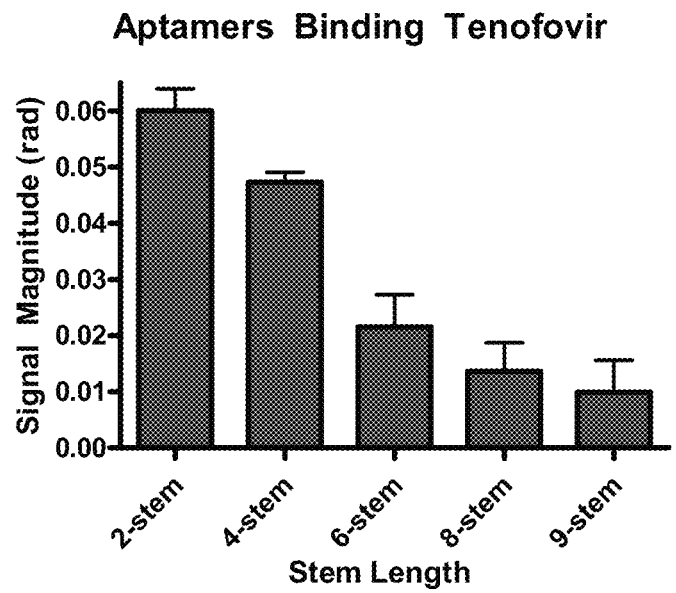
FIG. 2 illustrates the BSI signal magnitude of a hairpin aptamers binding to tenofovir with varying stem region length.

The Gibbs free energy ($\Delta G$) and melting temperature (Tm) of tenofovir aptamers with constant binding regions and varying stem lengths was calculated using Mfold® software. The $\Delta G$ and Tm both decrease as the length of the hairpin decreases, confirming the idea that short hairpins dissociate relatively freely, allowing the aptamer to change to a conformation with a lower energy state, thus eliciting a large BSI signal which is generated, in part, by conformational changes. As illustrated in FIG. 2 with tenofovir binding hairpin aptamers with constant binding regions and with varying stem lengths. Conversely, the aptamers with longer hairpins have a high $\Delta G$ and Tm, making it unlikely that the hairpin would dissociate upon binding to tenofovir, preventing a large conformational change from taking place.

Example of a Locked Hairpin Aptamer System Binding to Tenofovir

To further demonstrate the influence of the stem region hybridization, a variant of the tenofovir aptamer was designed having a very short stem, but with a photo-reactive crosslinker. Briefly, following incorporation of the so-called CNVK synthetic nucleotide during oligonucleotide synthesis, the aptamer was folded by heating to 85 degrees C., annealed slowly to room temperature, and finally irradiated with intense ultraviolet light (366 nm) for 1-2 seconds to create a covalent bond between the stem nucleotides to disable dehybridization. BSI studies were then performed using the "locked" tenofovir construct. The large BSI signal for the "2-stem" aptamer as illustrated in FIG. 2 resulting from the ability for large conformational change was largely lost from the "locked" conformation.

Example of a Hairpin Aptamer System Binding to P24

Figure 3:
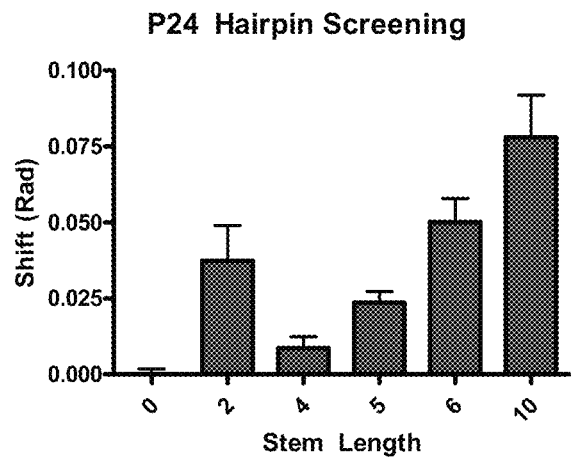
FIG. 3 illustrates the BSI signal magnitude of a hairpin aptamers binding to P24 with varying stem region length.

A system of hairpin aptamers was developed to bind to the HIV capsid protein p24. The signal for each aptamer was determined by incubating two concentrations of p24 (0 and 50 nM) with 50 nM aptamers. This data is shown in FIG. 3, and the signal-to-noise ratios of these assays are in Table 1, below:

TABLE 1

| 2-stem | 1.84 |
|---|---|
| 4-stem | 1.31 |
| 5-stem | 3.82 |
| 6-stem | 3.72 |
| Full Length | 3.24 |

This aptamer/protein set showed opposite results from the tenofovir system. Whereas in the tenofovir system shorter stem lengths gave larger signal, in the p24 system longer stem lengths showed larger signal. Without being bound to any particular theory, this may be due to tenofovir being a small molecule that binds somewhere in the loop, thus resulting in it not requiring the hairpin to disassociate to bind with the aptamer. However, shorter hairpins are more likely to dissociate, show a larger conformational change, and thus yield a larger BSI signal. P24 is a protein and because it is a much larger molecule it may force the hairpin to disassociate to bind. Because of this forced dissociation, longer hairpin regions would mean that more Watson-Crick pairings would be broken, eliciting a greater change in conformation and waters of hydration, giving a larger BSI signal.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A non-labeled molecular beacon comprising:
a hairpin aptamer having a non-self-hybridizing loop region and self-hybridizing stem region, said hairpin aptamer comprising a non-naturally occurring sequence comprising the sequence of SEQ ID No. 1;
wherein said self-hybridizing stem region dehybridizes upon binding of said hairpin aptamer to a target molecule to elicit a conformational change in said hairpin aptamer.

2. The non-labeled molecular beacon of claim 1, wherein said self-hybridizing stem has a hybridized length of between 2 and 6 nucleopairs.

3. The non-labeled molecular beacon of claim 1, wherein said self-hybridizing stem comprises at least one modulating feature.

4. The non-labeled molecular beacon of claim 3, wherein said at least one modulating feature selected from the group consisting of mismatch pair and accessory loop formation.

5. The non-labeled molecular beacon of claim 1, wherein said non-self-hybridizing loop region comprises an aptamer binding region with a specific binding affinity to said target molecule.

6. The non-labeled molecular beacon of claim 1, wherein said hairpin aptamer comprises at least one modified nucleotide.

7. The non-labeled molecular beacon of claim 1, wherein said hairpin aptamer binds to tenofovir.

* * * * *

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Aptamer sequence binding to tenofovir.

<400> SEQUENCE: 1
cgaaaactag acagcg                                              16